United States Patent [19]

Hamamura et al.

[11] Patent Number: 5,073,659
[45] Date of Patent: Dec. 17, 1991

[54] PROCESS FOR THE PREPARATION OF TERPENES

[75] Inventors: Kichisaburo Hamamura, Chiba; Yutaka Ohnuki, Aichi; Yukio Narabe, Ibaraki; Yoshihiro Hisatake, Ibaraki; Takashi Banba, Ibaraki; Shizumasa Kijima, Chiba, all of Japan

[73] Assignee: Eisai Co., Ltd., Tokyo, Japan

[21] Appl. No.: 565,569

[22] Filed: Aug. 10, 1990

[30] Foreign Application Priority Data

Aug. 22, 1989 [JP] Japan ................................. 1-215736
Nov. 1, 1989 [JP] Japan ................................. 1-285633

[51] Int. Cl.$^5$ ............................................. C07C 2/00
[52] U.S. Cl. ..................................... 585/600; 549/407; 560/127; 568/408; 568/417; 570/189; 570/217; 585/641
[58] Field of Search ................ 585/600, 641; 549/407; 560/129; 568/408, 417; 570/189, 217

[56] References Cited

U.S. PATENT DOCUMENTS 4,168,271 9/1979 Cardenas et al. .................... 585/600
4,292,459 9/1981 Cardenas et al. .................... 585/641

*Primary Examiner*—Curtis R. Davis
*Attorney, Agent, or Firm*—Flynn, Thiel, Boutell & Tanis

[57] ABSTRACT

A terpene compound having the formula (III) is produced by reacting an allylic halide having the formula (I) with a Grignard reagent having the formula (II) in the presence of anhydrous zinc chloride and a copper compound or an organic zinc halide compound having the formula (IV) in the presence of a copper compound, provided that when A-A is C-C, R' is hydrogen and when A-A is CC, X is chlorine.

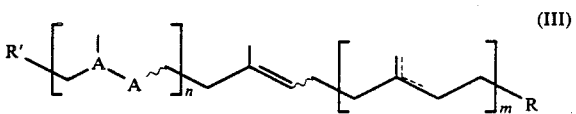

(III)

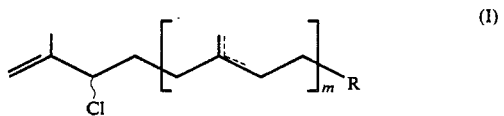

(I)

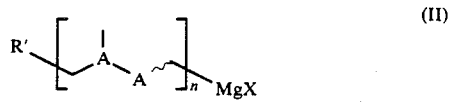

(II)

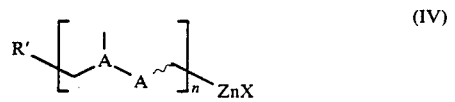

(IV)

6 Claims, No Drawings

PROCESS FOR THE PREPARATION OF TERPENES

FIELD OF INDUSTRIAL APPLICATION

The present invention relates to a novel process for the preparation of industrially useful terpenes.

PRIOR ART

Terpenes, which have been reported to exhibit various physiological effects represented by an in vivo antioxidant effect and therefor have recently been noted, are widely used not only in themselves but also as intermediates of drugs, foods and so on, thus being extremely important substances.

There have been made various studies and proposals on the preparation of terpenes.

Since compounds represented by the general formula:

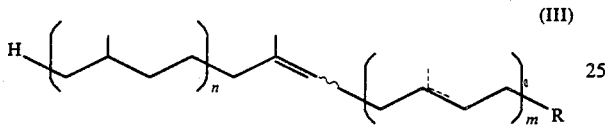

[wherein R represents a group represented by the formula:

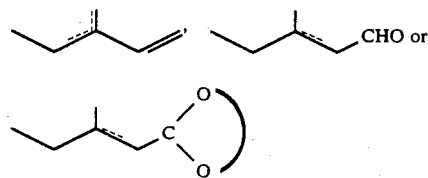

(wherein the

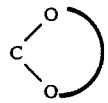

group represents a heterocyclic group containing two oxygen atoms as heteroatoms), a group represented by the formula:

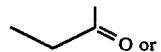

or

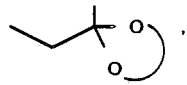

a hydroxyl group, a group represented by the formula: $-OR_1$ (wherein $R_1$ represents an acetyl (Ac) group, a $-COC_2H_5$ group or a benzyl, methoxymethyl or tetrahydro furfuryl group), a group represented by the formula:

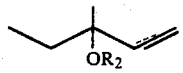

(wherein $R_2$ represents a hydrogen atom or an Ac group), a group represented by the formula:

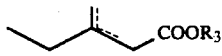

(wherein $R_3$ represents a hydrogen atom or a methyl or ethyl group), a group represented by the formula:

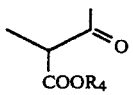

(wherein $R_4$ represents a methyl or ethyl group), a group represented by the formula:

(wherein $R_5$ and $R_6$ may be the same or different from each other and each represent a hydrogen atom or a methyl ethyl or isopropyl group), a group represented by the formula:

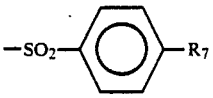

(wherein $R_7$ represents a hydrogen atom or a methyl group) or a group represented by the formula:

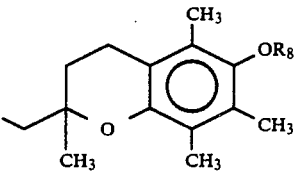

(wherein $R_8$ represents a hydrogen atom or a hydroxyl-protective group); m represents 0 to 3 and n represents 1 to 3] are each used as an intermediate or precursor in the preparation of a vitamin or a perfume, they are required to have high purities. However, no satisfactorily high-purity product can be obtained by the process of the prior art.

For example, U.S. Pat. Nos. 4,168,271 and 4,292,459 disclose the cross coupling reaction of an allylic chloride with a Grignard reagent. Although this reaction is conducted in the presence of a catalyst selected from among inorganic salts and complex salts of copper, iron, nickel and cobalt, the conversion of the allylic chloride is as low as 60 to 70%.

To show an instance, the reaction of 3,7-dimethyloctylmagnesium chloride with 3-chloromyrcene(3-chloro-6-methylene-2-methyloctadiene-1,7) in the presence of a copper catalyst gives 3-methylene-7,11,15-trimethyl-1,6-hexadecadine (γ-adduct) in a yield of 68% and the product contains 7 to 8% of an isomeric by-product (α-adduct) (see Comparative Example 1 which will be described below).

Further, French Patent No. 8,414,426 and Japanese Patent Laid-Open Nos. 112069/1986 and 118332/1986 disclose that the cross coupling reaction of a magnesium compound of 1,7-dichloro-3,7-dimethyloct-2-ene with 3-chloromyrcene in the presence of a copper catalyst gives 15-chloro-3-methylene-7,11,15-trimethylhexadeca-1,6,10-triene (γ-adduct) at a conversion of 3-chloromyrcene of 69% and that the product contains 6 to 8% of the α-adduct. When α-tocopherol (final product) is prepared by the use of each of the products of these processes as an intermediate, the above isomer ratio is retained as such to give a final product containing 6 to 8% of an isomeric by-product derived from the α-adduct.

As described above, the process of the prior art gives an isomeric by-product in addition to the objective compound, so that the establishment of a process for preparing such an intermediate or precursor

SUMMARY OF THE INVENTION

In view of the above problem, the inventors of the present invention have made, for a long time, intensive studies on the industrial process for the preparation of a terpene represented by the above general formula (III) which serves as an important intermediate for the preparation of a drug, a perfume or the like and have found that a high-purity terpene can be prepared by a process wherein the generation of the isomeric by-product (α-product) is inhibited by enhancing the regioselectivity of the cross coupling reaction to thereby obtain only the objective compound (γ-adduct), i.e., a process which comprises reacting a Grignard reagent with anhydrous zinc chloride to obtain an active alkylzinc halide and regioselectively cross-coupling this active alkylzinc halide with an allylic chloride in the presence of a copper compound. The present invention has been accomplished on the basis of this finding.

The invention provides a process for producing a terpene compound having the formula (III), which comprises reacting an allylic halide having the formula (I) with a Grignard reagent having the formula (II) in the presence of anhydrous zinc chloride and a copper compound or an organic zinc halide compound having the formula (IV) in the presence of a copper compound, provided that when A-A is C-C, R' is hydrogen and when A-A is C=C, X is chlorine.

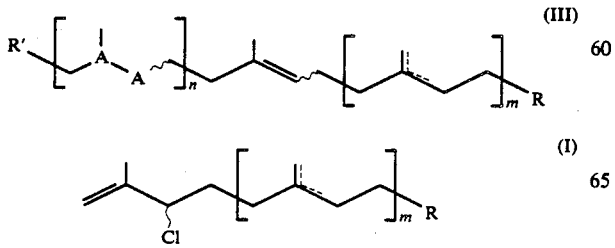

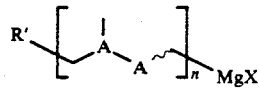

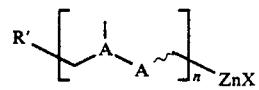

[wherein R represents a group represented by the formula:

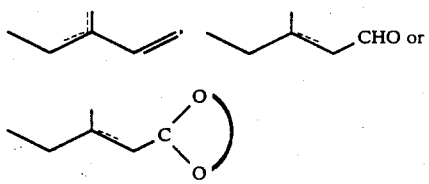

(wherein the

group represents a heterocyclic group containing two oxygen atoms as heteroatoms), a group represented by the formula:

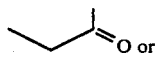

or

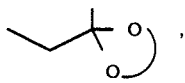

a hydroxyl group, a group represented by the formula: -OR$_1$ (wherein R$_1$ represents an acetyl (Ac) group, a propionyl group or a benzyl, methoxymethyl or tetrahydrofurfuryl group), a group represented by the formula:

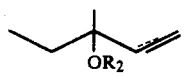

(wherein R$_2$ represents a hydrogen atom or an Ac group), a group represented by the formula:

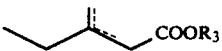

(wherein R$_3$ represents a hydrogen atom or a methyl or ethyl group), a group represented by the formula:

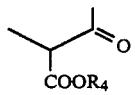

(wherein R₄ represents a methyl or ethyl group), a group represented by the formula:

(wherein R₅ and R₆ may be the same or different from each other and each represent a hydrogen atom or a methyl ethyl or isopropyl group), a group represented by the formula:

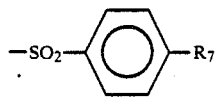

(wherein R₇ represents a hydrogen atom or a methyl group) or a group represented by the formula:

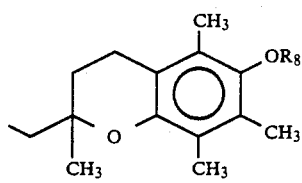

(wherein R₈ represents a hydrogen atom or a hydroxyl-protective group); R' represents a hydrogen atom or a straight-chain or branched alkyl, alkoxyalkyl, aralkyl, cyclic alkyl or halogen-substituted alkyl group; m represents 0 to 3, n is 1 to 3, A-A is C-C or C=C and X is bromine or chlorine.]

It is preferable that the copper compound is present in an amount of $10^{-5}$ to $10^{-1}$ gram atom per reaction equivalent and is selected from inorganic copper salts, organic copper salts and copper complex salts.

The process of the invention includes two embodiments in which A-A is C-C and C=C, respectively. Each embodiment will be illustrated below.

THE FIRST EMBODIMENT OF C-C FOR A-A

Namely, the present invention provides a process for the preparation of a terpene represented by the general formula:

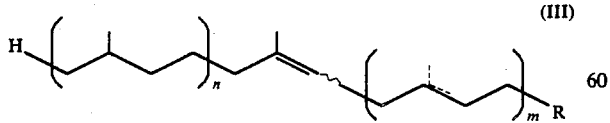

[wherein R represents a group represented by the formula:

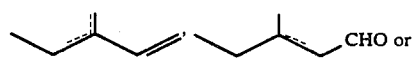

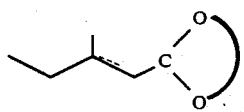

(wherein the

group represents a heterocyclic group containing two oxygen atoms as heteroatoms), a group represented by the formula:

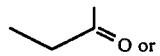

or

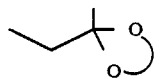

a hydroxyl group, a group represented by the formula: $-OR_1$ (wherein $R_1$ represents an acetyl (Ac) group, a $-COC_2H_5$ group or a benzyl, methoxymethyl or tetrahydrofurfuryl group), a group represented by the formula:

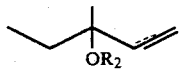

(wherein R₂ represents a hydrogen atom or an Ac group), a group represented by the formula:

(wherein R₃ represents a hydrogen atom or a xethyl or ethyl group), a group represented by the formula:

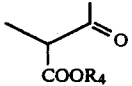

(wherein R₄ represents a methyl or ethyl group), a group represented by the formula:

(wherein R₅ and R₆ may be the same or different from each other and each represent a hydrogen atom or a methyl ethyl or isopropyl group), a group represented by the formula:

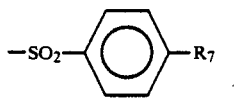

(wherein R$_7$ represents a hydrogen atom or a methyl group) or a group represented by the formula:

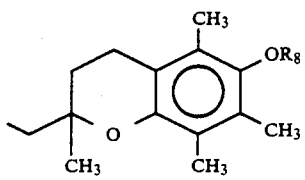

(wherein R$_8$ represents a hydrogen atom or a hydroxyl-protective group); m represents 0 to 3 and n represents 1 to 3] which comprises reacting an allylic chloride represented by the general formula:

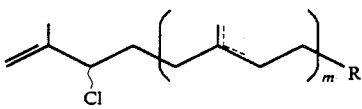

(I)

(wherein R and m are each as defined above), with a Grignard reagent represented by the general formula:

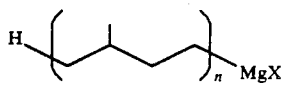

(II)

(wherein X represents a chlorine or bromine atom and n is as defined above), characterized by conducting said reaction in the presence of anhydrous zinc chloride and a copper compound.

In each formula of this specification, the symbol

represents a single or double bond, the symbol represents a double or triple bond and the symbol

∼ represents a cis or trans bond.

According to the present invention, it is particularly preferable in the preparation of a compound represented by the above general formula (III) by the reaction of an allylic chloride represented by the general formula (I) with a Grignard reagent represented by the general formula (II) that the Grignard reagent represented by the general formula (II) be preliminarily reacted with anhydrous zinc chloride to form an active alkylzinc halide represented by the general formula:

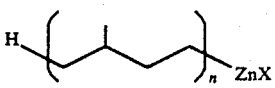

(IV)

wherein X and n are each as defined above, followed by the reaction of the active alkylzinc halide with the allylic chloride in the presence of a copper compound.

The reaction of an allylic chloride with a Grignard reagent is disclosed in U.S. Pat. Nos. 4,168,271 and 4,292,459 and French Patent No. 8,414,426. The cross coupling reaction of an allylic chloride with a Grignard reagent unavoidably gives an isomeric by-product, i.e., an α-adduct. In view of this problem, the inventors of the present invention have studied to obtain a reagent more active than a Grignard reagent and have found that an alkylzinc halide is excellent in reactivity. The present invention has been accomplished on the basis of this finding by utilizing a known reaction represented by the formula:

$$R'MgX + ZnCl_2 \rightarrow R'ZnCl + MgXCl$$

(see Basic Organometallic Chemistry, Walter de Gruyten, p. 70, 1985).

According to the present invention, a Grignard reagent represented by the general formula (II) is preliminarily reacted with anhydrous zinc chloride in an ether solvent at a temperature of $-70°$ to $120°$ C. to give an active alkylzinc halide, which is regioselectively cross-coupled with an allyl chloride represented by the general formula (I) in the presence of a copper compound.

When a compound of the general formula (III) is prepared according to the present invention, the obtained product contains only at most 0.6% of an isomeric by-product, i.e., an α-adduct represented by the general formula (V):

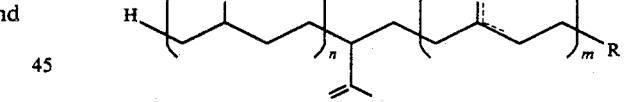

(V)

wherein R, m and n are each as defined above. The conversion of the allyl chloride into the γ-adduct which is the objective compound of the present invention is 95% or above and the content of a remaining unreacted allylic chloride is 5% or below. The isolation yield is 60 to 95%.

The copper compound to be used in the present invention may be an inorganic or organic copper salt or a copper complex salt selected, from among CuI, CuBr, CuI·P(C$_2$H$_5$)$_3$, CuI·P(C$_6$H$_5$)$_3$, CuBr·(CH$_3$)$_2$S, CuCl, CuCl$_2$, Cu(CH$_3$COCH$_2$COO)$_2$ and Li$_2$CuCl$_4$. Particularly CuI·P(C$_6$H$_5$)$_3$ and CuBr (CH$_3$)$_2$S are preferred.

The amount of the copper compound used is preferably $10^{-5}$ to $10^{-1}$, still preferably 0.001 to 0.05 gram atom per reaction equivalent.

Examples of the allylic chloride represented by the general formula (I) include the following groups of compounds:

(1) a group of compounds each represented by the general formula (I) wherein m is 0 to 1 and R is

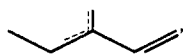

which are derived from myrcene, ocimene, citronellene and β-farnesene, (2) a group of compounds each represented by the general formula (I) wherein m is 0 to 1 and R is a group represented by the formula:

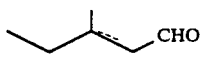

or

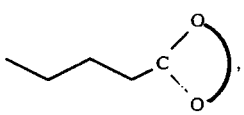

which are derived from citral, citronellal, farnesal and derivatives thereof having a protected aldehyde group, (3) a group of compounds each represented by the general formula (I) wherein m is 0 to 1 and R is a group represented by the formula:

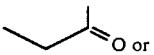

or

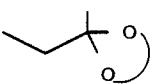

which are derived from methylheptenone, geranylacetone nerylacetone and derivatives thereof having a protected keto group, (4) a group of compounds each represented by the general formula (I) wherein m is 1 to 2 and R is an OH group or a group represented by the formula: $OR_1$ (wherein $R_1$ is an Ac group, a $COC_2H_5$ group or a benzyl, methoxymethyl or tetrahydrofurfuryl group), which are derived from geraniol, nerol, farnesol and acetates and ethers thereof, (5) a group of compounds each represented by the general formula (I) wherein m is 0 to 1 and R represents a group represented by the formula:

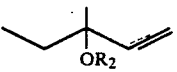

(wherein $R_2$ represents a hydrogen atom or an Ac group), which are derived from nerol, dehydronerol, nerolidol, dehydronerolidol and acetates thereof, (6) a group of compounds each represented by the general formula (I) wherein m is 0 to 1 and R represents a group represented by the formula:

(wherein $R_3$ represents a hydrogen atom or a methyl or ethyl group), which are derived from geranic acid, γ-geranic acid, farnesic acid and esters thereof, (7) a group of compounds each represented by the general formula (I) wherein m is 0 to 1 and R represents a group represented by the formula:

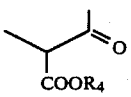

(wherein $R_4$ represents a methyl or ethyl group), which are derived from keto carboxylic acid derivatives prepared by the coupling of prenyl chloride, geranyl chloride or neryl chloride with an acetoacetic ester, (8) a group of compounds each represented by the general formula (I) wherein m is 0 to 2 and R represents a group represented by the formula:

(wherein $R_5$ and $R_6$ may be the same or different from each other and each represents a hydrogen atom or a methyl, ethyl or isopropyl group), which are derived from prenylamine, geranylamine, nerylamine, farnesylamine and dialkylamine derivatives thereof, (9) a group of compounds each represented by the general formula (I) wherein m is 0 to 2 and R represents a group represented by the formula:

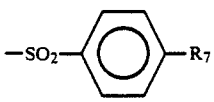

(wherein $R_7$ represents a hydrogen atom or a methyl group), which are derived from prenyl sulfone derivatives, geranyl sulfone derivatives, neryl sulfone derivatives and farnesyl sulfone derivatives, and

(10) a group of compounds each represented by the general formula (I) wherein m is 0 and R represents a group represented by the formula:

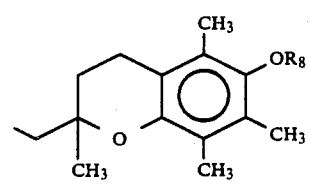

(wherein $R_8$ represents a hydrogen atom or a hydroxyprotective group), which are derived from 2,5,7,8-tetramethyl-2-(4'-methyl-3'-pentenyl)-6- chromanol and derivatives thereof having a protected ether linkage.
Particular examples of the allylic chloride include those represented by the following structural formulas:
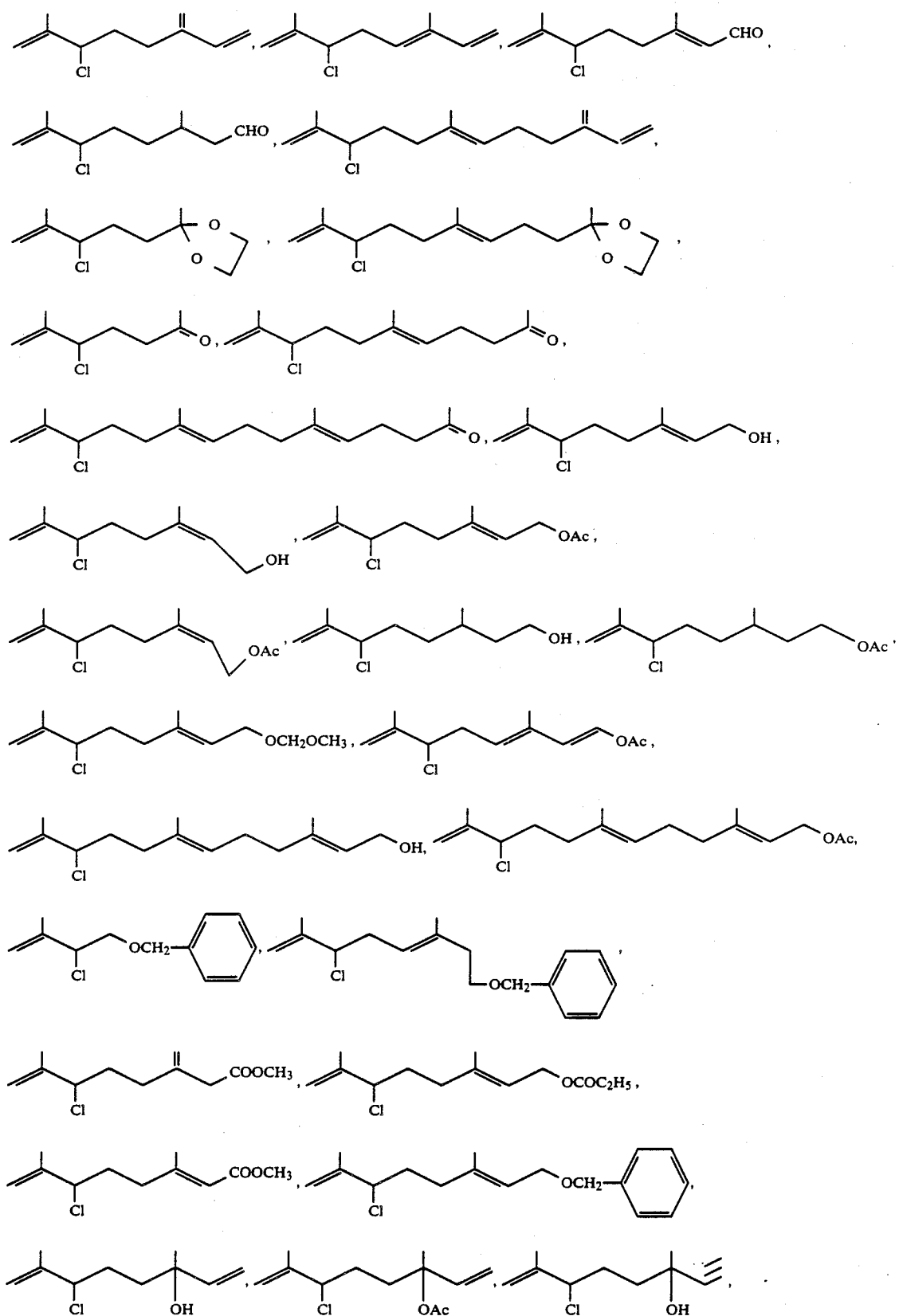

-continued

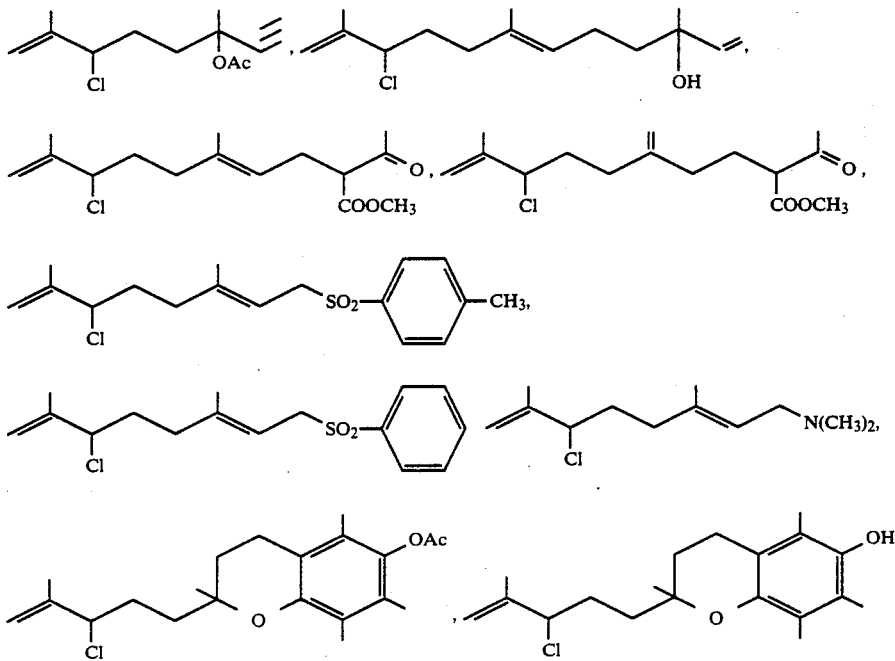

The solvent to be used in the reaction according to the present invention may be an ether such as diethyl ether or tetrahydrofuran alone or a mixture thereof with a nonpolar solvent such as n-hexane, toluene or benzene.

The above series of reactions of the compound of the present invention will now be described in detail.

A Grignard reagent preliminarily prepared is put in a reactor filled with an inert gas such as nitrogen or argon. Anhydrous zinc chloride is introduced into the reactor at a temperature of −70° to 120° C., preferably −20° to 20° C. in the absence or presence of an ether solvent such as tetrahydrofuran to carry out a reaction. Thus, an alkylzinc halide is formed. Then, a copper compound and a solution of an allylic chloride in an inert solvent are introduced into the reactor successively to carry out further reaction. After sopping of the reaction, the contents are taken out of the reactor and extracted with a suitable solvent. The extract is purified by distillation or column chromatography to isolate a pure terpene.

According to the present invention, a high purity terpene can be obtained in an extremely high yield. Further, various useful compounds can be prepared each in a high yield and at a high purity by using the terpene prepared by the process of the present invention as a starting material. For example, when Vitamin E, which exhibits various effects such as antioxidant and lipometabolism-improving effects, is prepared by using a terpene prepared by the process of the present invention as a starting material, it can be obtained in a high yield and at a high purity. Particularly, as will be described in Example 24, a Vitamin-related compound having a purity of at least 98% can be obtained in a yield of at least 95%. On the other hand, the Grignard process of the prior art (disclosed in the U.S. Pat. Nos. 4,168,271 and 4,292,459) gave a yield of 80% and a purity of 92%. Thus, the process of the present invention can give the objective compound at an enhanced purity and in an enhanced yield, being highly useful.

THE SECOND EMBODIMENT OF C=C FOR A-A

Namely, the present invention provides a process for the preparation of an unsaturated terpene represented by the general formula:

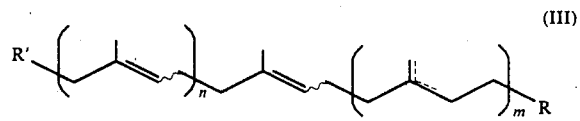

[wherein R represents a group represented by the formula:

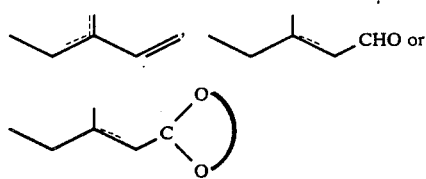

(wherein the

group represents a heterocyclic group containing two oxygen atoms as heteroatoms), a group represented by the formula:

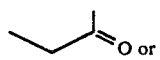

or

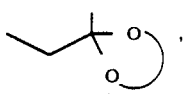

a hydroxyl group, a group represented by the formula: $-OR_1$ (wherein $R_1$ represents an acetyl (Ac) group, a propionyl group or a benzyl, methoxymethyl or tetrahydrofurfuryl group), a group represented by the formula:

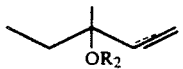

(wherein $R_2$ represents a hydrogen atom or an Ac group), a group represented by the formula:

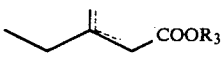

(wherein $R_3$ represents a hydrogen atom or a methyl or ethyl group), a group represented by the formula:

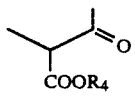

(wherein $R_4$ represents a methyl or ethyl group), a group represented by the formula:

(wherein $R_5$ and $R_6$ may be the same or different from each other and each represent a hydrogen atom or a methyl ethyl or isopropyl group), a group represented by the formula:

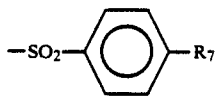

(wherein $R_7$ represents a hydrogen atom or a methyl group) or a group represented by the formula:

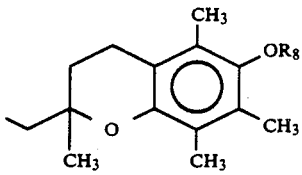

(wherein $R_8$ represents a hydrogen atom or a hydroxyl-protective group); R' represents a hydrogen atom or a straight-chain or branched alkyl, alkoxyalkyl, aralkyl, cyclic alkyl or halogen-substituted alkyl group preferably having 5 to 10 carbon atoms; m represents 0 to 3 and n represents 1 to 3] which comprises reacting an allylic chloride represented by the general formula:

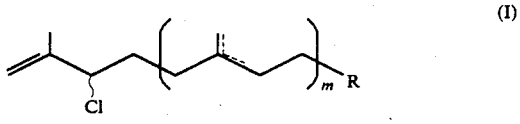

(wherein R and m are each as defined above), with a Grignard reagent represented by the general formula:

(wherein R' and n are each as defined above), characterized by conducting said reaction in the presence of anhydrous zinc chloride and a copper compound.

In each formula of this specification, the symbol

----- represents a single or double bond, the symbol

===== represents a double or triple bond and the symbol

∼ represents a cis or trans bond.

According to the present invention, it is particularly preferable in the preparation of a compound represented by the above general formula (III) by the reaction of an allylic chloride represented by the general formula (I) with a Grignard reagent represented by the general formula (II) that the Grignard reagent represented by the general formula (II) be preliminarily reacted with anhydrous zinc chloride to form an active allylzinc chloride represented by the general formula:

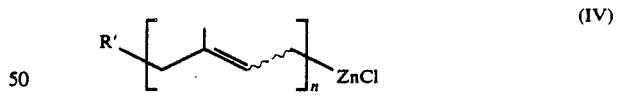

wherein R' and n are each as defined above, followed by the reaction of the active allylzinc chloride with the allylic chloride in the presence of a copper compound.

The reaction of an allylic chloride with a Grignard reagent is disclosed in U.S. Pat. Nos. 4,168,271 and 4,292,459 and French Patent No. 8,414,426. The cross coupling reaction of an allylic chloride with a Grignard reagent unavoidably gives an isomeric by-product, i.e., an α-adduct. In view of this problem, the inventors of the present invention have studied to obtain a reagent more active than a Grignard reagent and have found that an allylzinc chloride is excellent in reactivity. The present invention has been accomplished on the basis of this finding by utilizing a known reaction represented by the formula:

R''MgX + ZnCl$_2$ → R''ZnCl + MgXCl (see Basic Organometallic Chemistry, Walter de Gruyten, p. 70, 1985).

According to the present invention, a Grignard reagent represented by the general formula (II) is preliminarily reacted with anhydrous zinc chloride in an ether solvent at a temperature of −70° to 20° C. to give an active allylzinc chloride, which is regioselectively cross-coupled with an allylic chloride represented by the general formula (I) in the presence of a copper compound.

When a compound of the general formula (III) is prepared according to the present invention, the obtained product contains only at most 0.5% of an isomeric by-product, i.e., an α-adduct represented by the general formula (V):

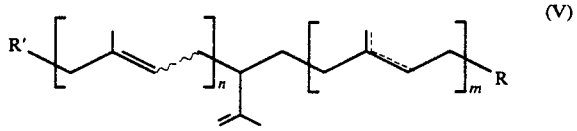

(V)

wherein R, R', m and n are each as defined above. The conversion of the allylic chloride into the γ-adduct which is the objective compound of the present invention is 97% or above and the content of a remaining unreacted allylic chloride is 3% or below. The isolation yield is 70 to 95%.

Examples of the compound represented by the above general formula (II) to be used in the present invention include geranylmagnesium chloride, prenylmagnesium chloride, nerylmagnesium chloride, 6,7-dihydrogeranylmagnesium chloride, 7-chloro-3,7-dimethyloct-2(E)-enyl-1-magnesium chloride, farnesylmagnesium chloride, nerolidylmagnesium chloride, 6,7-dihydrofarnesylmagnesium chloride, 10,11-dihydrofarnesylmagnesium chloride and 6,7,10,11-tetrahydrofarnesylmagnesium chloride.

The above series of reactions of the compound of the present invention will now be described in detail.

A Grignard reagent preliminarily prepared is put in a reactor filled with an inert gas such as nitrogen or argon. Anhydrous zinc chloride is introduced into the reactor at a temperature of −70° to 20° C., preferably −20° to 20° C. in the absence or presence of an ether solvent such as tetrahydrofuran to carry out a reaction. Thus, an allylzinc chloride is formed. Then, a copper compound and a solution of an allylic chloride in an inert solvent are introduced into the reactor successively to carry out further reaction. After stopping the reaction, the contents are taken out of the reactor and extracted with a suitable solvent. The extract is purified by distillation or column chromatography to isolate a pure unsaturated terpene.

According to the present invention, a high-purity unsaturated terpene can be obtained in an extremely high yield. Further, various useful compounds can be prepared each in a high yield and at a high purity by using the unsaturated terpene prepared by the process of the present invention as a starting material. For example, when Vitamin E, which exhibits various effects such as antioxidant and lipometabolism-improving effects, is prepared by using an unsaturated terpene prepared by the process of the present invention as a starting material, it can be obtained in a high yield and at a high purity. Particularly, as will be described in Example 38, a Vitamin E-related compound having a purity of at least 98% can be obtained in a yield of at least 95%. On the other hand, the Grignard process of the prior art (disclosed in the U.S. Pat. Nos. 4,168,271 and 4,292,459) gave a yield of 80% and a purity of 92%. Thus, the process of the present invention can give the objective compound at an enhanced purity and in an enhanced yield, being highly useful.

The explanation about the compound (I), the catalyst and the solvent, shown in the first embodiment, is applied to the second embodiment.

EXAMPLE

The present invention will now be described in more detail by referring to the following Examples, though it is a matter of course that the present invention is not limited to them only.

Comparative Example 1 gives the results of the follow-up of the preparation of 3-methylene-7,11,15-trimethyl-16-hexadecadiene, which is the same compound as that prepared in Example 1, according to a known process (described in the U.S. Pat. Nos. 4,168,271 and 4,292,489).

EXAMPLE 1

Synthesis of 3-methylene-7,11,15-trimethyl-1,6-hexadecadiene

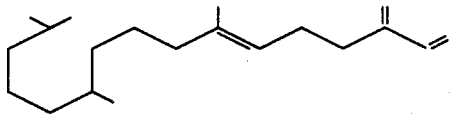

33 g (0.15 mol) of 3,7-dimethyloctyl bromide, 3.65 g of metallic magnesium and 400 ml of tetrahydrofuran were introduced into a 1-l four-necked flask purged with argon gas, followed by the addition of five droplets of ethylene dibromide as a reaction initiator. The contents were stirred under reflux for 2 hours to carry out a reaction. Thereby, the metallic magnesium was dissolved to give a solution of 3,7-dimethyloctylmagnesium bromide in tetrahydrofuran.

This solution was gradually cooled to 18° C. in an argon stream, followed by the addition of 20 g (0.15 mol) of anhydrous zinc chloride. The obtained mixture was vigorously stirred for one hour. The mixture gradually turned cloudy to give a tetrahydrofuran solution of 3,7-dimethyloctylzinc chloride.

1 g (0.0048 mol) of CuBr·(CH$_3$)$_2$S was added to this solution and the obtained mixture was stirred for 30 minutes. The cloudy solution gradually turned dark gray. 200 ml of a solution of 17 g (0.07 mol) of 3-chloro-6-methylene-2-methyloctadiene-1,7 having a purity of 70% in tetrahydrofuran was gradually dropped into the solution over a period of 30 minutes, followed by stirring at a room temperature for 3 hours. After the confirmation of the disappearance of the raw material by TLC and HPLC, 500 ml of a saturated aqueous solution of ammonium chloride was dropped into the reaction system to stop the reaction.

The obtained reaction mixture was twice extracted each with 500 ml of n-hexane and the combined extracts were dried and freed from the solvent by distillation to give 36 g of a colorless liquid.

The crude product thus obtained had a ratio of the objective compound (γ-adduct) to an isomeric by-product (α-adduct) of 99.5: 0.5 as determined by HPLC. The conversion was 97.5%.

36 g of the above crude product was purified by column chromatography using 2.8 kg of 200-mesh silica gel and a single solvent system of n-hexane to give 14.4 g of the objective compound as a colorless liquid (yield: 74.4%, purity: 99.1%). elemental analysis: $C_{20}H_{36}$ (MW=276.508)

|  | C (%) | H (%) |
|---|---|---|
| calculated: | 86.88 | 13.12 |
| found: | 86.98 | 13.03 |

NMR (CDCl$_3$, δ); 6.3(d,d,1H), 4.9~5.4(m,5H)
Mass; M$^+$=276 elemental analysis: $C_{15}H_{26}$ (MW=206.378)

|  | C (%) | H (%) |
|---|---|---|
| calculated: | 87.30 | 12.70 |
| found: | 87.41 | 12.60 |

NMR (CDCl$_3$, δ); 6.3(d,d,1H), 4.9~5.4(m,5H)
Mass ; M$^+$=206

EXAMPLES 3 TO 18

The same procedure as that described in Example 1 was repeated except that the kind and molar ratio of the catalyst, the solvent and the reaction conditions were varied as specified in Table 1 respectively. The results are given in Table 1.

TABLE 1

| Example No. | Zinc compound | Allylic chloride | Catalyst/(mol %) | Solvent | Reaction condition (°C./hr) | Conversion* (%) | Product (α/γ) |
|---|---|---|---|---|---|---|---|
| 3 | 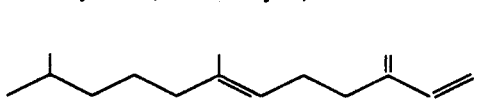 | 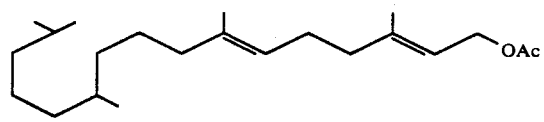 | CuI/5 | tetrahydrofuran (THF) | room temp./2 | 95 | 0.5/99.5 |
| 4 | | | CuBr/5 | tetrahydrofuran (THF) | room temp./1 | 95 | 0.6/99.4 |
| 5 | | | CuCl/5 | tetrahydrofuran (THF) | room temp./1 | 95 | 0.3/99.7 |
| 6 | | | CuCl$_2$/5 | tetrahydofuran (THF) | room temp./1 | 95 | 0.5/99.5 |
| 7 | | | Cu(CH$_3$CHCH$_2$COO)$_2$/5 | tetrahydofuran (THF) | room temp./2 | 95 | 0.6/99.4 |
| 8 | | | CuI.(C$_6$H$_5$)$_3$P/5 | tetrahydofuran (THF) | room temp./3 | 95 | 0.3/99.7 |
| 9 | | | CuBr.(CH$_3$)$_2$S/5 | tetrahydofuran (THF) | room temp./2 | 95 | 0.2/99.8 |
| 10 | | | CuBr.(CH$_3$)$_2$S/10 | tetrahydofuran (THF) | room temp./1 | 95 | 0.5/99.5 |
| 11 | | | CuBr.(CH$_3$)$_2$S/1 | tetrahydofuran (THF) | room temp./4 | 95 | 0.6/99.4 |
| 12 | | | CuBr.(CH$_3$)$_2$S/5 | diethyl ether | room temp./5 | 83 | 0.6/99.4 |
| 13 | | | CuBr.(CH$_3$)$_2$S/5 | hexane-THF | room temp./1 | 95 | 0.4/99.6 |
| 14 | | | CuBr.(CH$_3$)$_2$S/5 | toluene-THF | room temp./1 | 95 | 0.5/99.5 |
| 15 | | | CuBr.(CH$_3$)$_2$S/5 | THF | 0/2 | 95 | 0.2/99.8 |
| 16 | | | LiCuCl$_4$/5 | " | room temp./5 | 90 | 0.6/99.4 |
| 17 | | | CuI.(C$_6$H$_5$)$_3$P/5 | " | room temp./2 | 95 | 0.3/99.7 |
| 18 | ![structure]ZnCl | | CuBr.(CH$_3$)$_2$S/5 | " | room temp./1 | 95 | 0.5/99.5 |

*Conversion: in terms of HPLC value (95 = 95 to 100%)

EXAMPLE 2

Synthesis of 3-methylene-7,11-dimethyl-1,6-dodecadiene

The same procedure as that described in Example 1 was repeated except that 22.6 g (0.15 mol) of 1-bromo-3-methylbutane, 3.65 g of metallic magnesium, 400 ml of tetrahydrofuran, five droplets of ethylene dibromide, 20 g (0.15 mol) of anhydrous zinc chloride, 2 g (0.01 mol) of CuBr·(CH$_3$)$_2$S, 17 g (0.07 mol) of 3-chloro-6-methylene-2-methyloctadiene-1,7 having a purity of 70%, 200 ml of tetrahydrofuran and 500 ml of a saturated aqueous solution of ammonium chloride were used. Thus, 12.0 g of the objective compound was obtained as a colorless liquid (yield: 83.2%).

This liquid had a ratio of the objective compound (γ-adduct) to an isomeric by-product (α-adduct) of 99.5 : 0.5 as determined by HPLC. The conversion was 98%.

EXAMPLE 19

Synthesis of 3,7,11,15-tetramethylhexadeca-2(E),6-dien-1-yl acetate

A tetrahydrofuran solution of 3,7-dimethyloctylmagnesium bromide was prepared from 6.64 g (0.03 mol) of 3,7-dimethyloctyl bromide, 0.73 g of metalic magnesium, 40 ml of tetrahydrofuran and 3 droplets of ethylene dibromide as a reaction initiator in a similar manner to that of Example 1. 4.08 g (0.03 mol) of anhydrous zinc chloride was added to the solution, while keeping the solution at 10° C. The obtained mixture was stirred for one hour to give a cloudy tetrahydrofuran solution of 3,7-dimethyloctylzinc chloride.

0.2 g (0.001 mol) of CuBr·(CH$_3$)$_2$S was added to this cloudy solution, followed by stirring for 30 minutes. 40 ml of a solution of 4.4 g (0.02 mol) of 6-chloro-7-methylene-3-methyl-2(E)-octen-1-yl acetate in tetrahydrofuran was dropped into the obtained mixture at 20° C. over a period of 30 minutes. After the completion of the dropping, the obtained mixture was stirred at 25° C. for 3 hours and subjected to TLC and HLPC to confirm the disappearance of the chlorine-containing raw material. 20 ml of a saturated aqueous solution of ammonium chloride was added to the reaction system to stop the reaction.

The reaction mixture was poured into 200 ml of ice-water and extracted with 100 ml of n-hexane. The extract was dried and freed from the solvent by distillation to give 8.2 g of a colorless liquid. This liquid was purified by column chromatography using 200 g of silica gel (200-mesh), n-hexane and benzene to give 4.4 g of the objective compound as a colorless liquid (yield: 65.5%).

elemental analysis: $C_{22}H_{40}O_2$ (MW=336.54)

|  | C (%) | H (%) |
|---|---|---|
| calculated: | 78.52 | 11.98 |
| found: | 78.72 | 11.96 |

IR (cm$^{-1}$); 1740 (OCOCH$_3$)

NMR (CDCl$_3$, δ); 5.4 (t, 1H), 5.2 (t, 1H), 4.6 (d, 2H), 2.05 (s, 3H)

Mass; M$^+$ =336

EXAMPLE 20

Synthesis of 3,7,11,15-tetramethylhexadeca-2(Z),6-dien-1-yl acetate

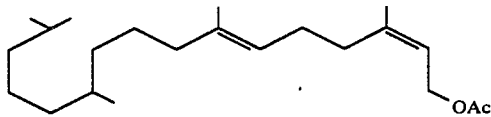

A tetrahydrofuran solution of 3,7-dimethyloctylmagnesium bromide was prepared from 6.64 g (0.03 mol) of 3,7-dimethyloctyl bromide, 0.73 g of metallic magnesium, 40 ml of tetrahydrofuran and 3 droplets of ethylene dibromide in a similar manner to that described in Example 1. 4.08 g (0.03 mol) of anhydrous zinc chloride was added to the solution to give a tetrahydrofuran solution of 3,7-dimethyloctylzinc chloride. The subsequent step was conducted with this solution, 0.2 g (0.001 mol) of CuBr·(CH$_3$)$_2$S and 4.4 g (0.02 mol) of 6-chloro-7-methylene-3-methyl-2(Z)-octen-1-yl acetate in a similar manner to that described in Example 20 to give 4.0 g of the objective compound as a colorless liquid (yield: 59.7%).

IR (cm$^{-1}$) : 1740 (OCOCH$_3$)

NMR (CDCl$_3$, δ); 5.4 (t, 1H), 5.25 (t, 1H), 4.6 (d, 2H), 2.0 (s, 3H)

Mass; M$^+$ =336

EXAMPLE 21

Synthesis of 3,7,11,15-tetramethylhexadeca-1,6-dien-3-yl acetate

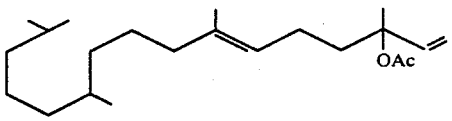

In a similar manner to that described in Example 1, a tetrahydrofuran solution of 3,7-dimethyloctylmagnesium bromide was prepared from 6.64 g (0.03 mol) of 3,7-dimethyloctyl bromide, 0.73 g of metallic magnesium, 40 ml of tetrahydrofuran and 3 droplets of ethylene bromide and converted into a tetrahydrofuran solution of 3,7-dimethyloctylzinc chloride by the addition of 4.08 g (0.03 mol) of anhydrous zinc chloride. The subsequent step was conducted with this solution, 0.2 g (0.001 mol) of CuBr·(CH$_3$)$_2$S and 4.4 g (0.02 mol) of 6-chloro-7-methylene-3-methyl-1-octen-3-yl acetate in a similar manner to that described in Example 20 to give 4.1 g of the objective compound as a colorless liquid (yield: 61.2%).

IR (cm$^{-1}$); 1740 (OCOCH$_3$)

NMR(CDCl$_3$, δ); 6.0 (d, d, 1H), 5.3~5.0 (m, 3H), 2.0 (s, 3H)

Mass; M$^+$ =336

EXAMPLE 22

Synthesis of 3,7,11,15-tetramethylhexadeca-2(E),6(E),10-trien-1-yl acetate

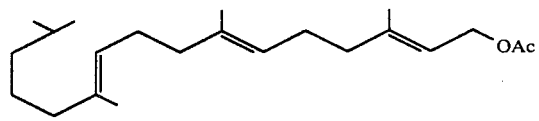

In a similar manner to that described in Example 1, a tetrahydrofuran solution of 3-methylbutylmagnesium bromide was prepared from 4.53 g (0.03 mol) of 1-bromo-3-methylbutane, 0.73 g of metallic magnesium, 40 ml of tetrahydrofuran and 3 droplets of ethylene dibromide and converted into a tetrahydrofuran solution of 3-methylbutylzinc chloride by the addition of 4.08 g (0.03 mol) of anhydrous zinc chloride. The subsequent step was conducted with this solution, 0.2 g (0.001 mol) of CuBr·(CH$_3$)$_2$S and 6.0 g (0.02 mol) of 10-chloro-11-methylene-3,7-dimethyl-2(E),6(E)-dodecadien-1-yl acetate in a similar manner to that described in Example 20 to give 3.8 g of the objective compound as a colorless liquid (yield: 56.8%).

elemental analysis: $C_{22}H_{38}O_2$ (MW=334.54)

|  | C (%) | H (%) |
|---|---|---|
| calculated: | 78.99 | 11.45 |
| found: | 79.12 | 11.50 |

IR (cm$^{-1}$); 1740 (OCOCH$_3$) NMR(CDCl$_3$, δ); 5.4 (t, 1H), 5.2 (t, 2H), 4.6 (d, 2H), 2.05 (s, 3H)

Mass; M$^+$ =334

Example 23

Synthesis of 3',4'-dehydro-α-tocopheryl benzyl ether

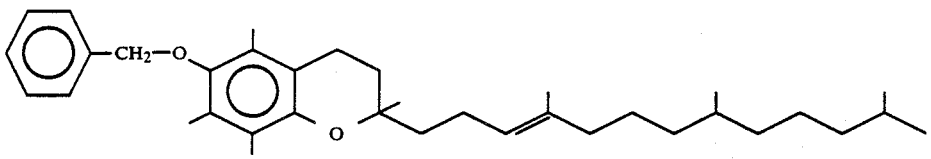

A Grignard reagent was prepared from 3.63 g (0.016 mol) of 3,7-dimethyloctyl bromide, 0.363 g (0.015 mol) of metallic magnesium, 40 ml of tetrahydrofuran and 3 droplets of ethylene dibromide as a reaction initiator. 2.09 g (0.015 mol) of anhydrous zinc chloride was added to the tetrahydrofuran solution of 3,7-dimethyloctyl-magnesium bromide, while keeping the solution at 20° C. The obtained mixture was stirred at that temperature for one hour to give a cloudy tetrahydrofuran solution of 3,7-dimethyloctylzinc chloride. 0.3 g (0.0007 mol) of $CuI \cdot (C_6H_5)_3P$ was added to this solution, followed by stirring for 5 minutes. 20 ml of a solution of 1.0 g (0.0024 mol) of 2,5,7,8-tetramethyl-2-(3'-chloro-4'-methylenepentyl)-6-yl benzyl ether having a purity of 98% in tetrahydrofuran was dropped into the obtained mixture at 20° C. over a period of 5 minutes. After the completion of the dropping, the obtained mixture was stirred at that temperature for 2 hours and subjected to TLC and HPLC to confirm the disappearance of the chlorine-containing raw material. The ratio of the γ-adduct to the α-adduct (γ:α) was 98:2 (conversion: 95%).

EXAMPLE 24

Synthesis of 2-(4,8,12-trimethyldodeca-3,7-dienyl)-2,4-dimethyl-1,3-dioxolane

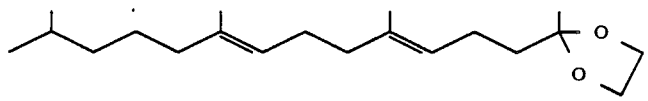

In a similar manner to that described in Example 1, a tetrahydrofuran solution of 3-methylbutylmagnesium bromide was prepared from 2.27 g (0.015 mol) of 1-bromo-3-methylbutane, 0.36 g of metallic magnesium, 40 ml of tetrahydrofuran and 3 droplets of ethylene dibromide and converted into a tetrahydrofuran solution of 3-methylbutylzinc chloride by the addition of 1.5 g (0.01 mol) of anhydrous zinc chloride. The subsequent step was conducted with this solution, 0.15 g (0.00075 mol) of $CuBr \cdot (CH_3)_2S$, 1.43 g of 2-(7-chloro-4,8-dimethyl-3,8-nonadienyl)-2,4-dimethyl-1,3-dioxolane and 20 ml of tetrahydrofuran to give 0.87 g of the objective compound as a colorless liquid (yield: 54%).

This liquid was deketalized according to a conventional method and catalytically reduced to form phytone, which was examined for the α-adduct content by GLC. The content was 0.5% or below.

COMPARATIVE EXAMPLE 1

Synthesis of 3-methylene-7,11,15-trimethyl-1,6-hexadecadiene

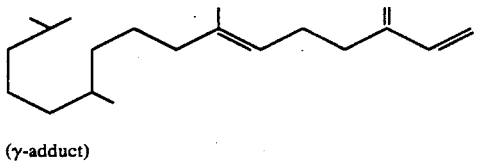

(γ-adduct)

A tetrahydrofuran solution of 3,7-dimethyloctylmagnesium bromide was prepared from 6.64 g (0.03 mol) of 3,7-dimethyloctyl bromide, 0.73 g of metallic magnesium, 50 ml of tetrahydrofuran and 3 droplets of ethylene dibromide in a similar manner to that described in Example 1 and cooled to 5° C., followed by the addition of 0.6 g (0.003 mol) of $CuBr \cdot (CH_3)_2S$. The obtained mixture was stirred at that temperature for 30 minutes. 50 ml of a solution of 3.4 g (0.02 mol) of 3-chloro-6-methylene-2-methyloctadiene-1,7 having a purity of 70% in tetrahydrofuran was dropped into the resulting mixture over a period of 30 minutes. After the completion of the dropping, the obtained mixture was stirred at that temperature for one hour and subjected to TLC and HPLC to confirm the disappearance of the chlorine-containing raw material.

At this point, the ratio of the objective compound (γ-adduct) to the isomeric by-product (α-adduct) was 91.6:8.4.

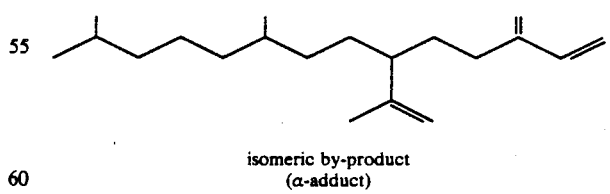

isomeric by-product
(α-adduct)

Comparative Example 2 gives the results of the follow-up of the preparation of 15-chloro-3-methylene-7,11,15-trimethylhexadeca-1,6,10(E)-triene, which is the same compound as that prepared in Example 47, according to a known process (described in the French Patent No. 8,414,426 and Japanese Patent Laid-Open Nos. 112069/1986 and 118332/1986).

EXAMPLE 25

Synthesis of 3-methylene-7,11,15-trimethyl-1,6,10(E),(14(E)-hexadecatetraene

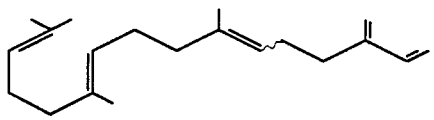

2.92 g of metallic magnesium, 200 ml of tetrahydrofuran and five droplets of ethylene dibromide were introduced into a 1-l-four-necked flask purged with argon gas. While the contents were stirred under cooling with a freezing mixture at −15° C., 100 ml of a tetrahydrofuran solution containing 29.6 g (0.12 mol) of geranyl chloride having a purity of 70% was gradually dropped into the flask over a period of 3 hours. After the completion of the dropping, the obtained mixture was stirred at that temperature for 2 hours to thereby dissolve the metallic magnesium. Thus, a light gray tetrahydrofuran solution of geranylmagnesium chloride was obtained.

10.9 g (0.08 mol) of anhydrous zinc chloride was added to this solution at −15° C. in an argon stream. The obtained mixture was vigorously stirred for 2 hours. The mixture gradually turned cloudy to finally give a semiopaque homogeneous tetrahydrofuran solution of geranylzinc chloride.

1 g (4 8 mmol) of CuBr·(CH$_3$)$_2$S was added to this solution and the obtained mixture was stirred for one hour. The semiopaque solution gradually turned dark gray. 200 ml of a solution of 19.5 g (0.08 mol) of 3-chloro-6-methylene-2-methyloctadiene-1,7 having a purity of 70% in tetrahydrofuran was gradually dropped into the solution over a period of 2 hours. After the completion of the dropping, the obtained mixture was stirred at −10° to −5° C. for 5 hours and heated to a room temperature. After the confirmation of the disappearance of the raw material by TLC and HPLC, 300 ml of a saturated aqueous solution of ammonium chloride was dropped into the mixture to stop the reaction. The obtained mixture was twice extracted each with 500 ml of n-hexane and the combined extracts were dried and freed from the solvent by distillation to give 39.3 g of a pale yellow liquid. The conversion as determined by HPLC or GLC was 99% or above.

The liquid obtained above was heated to 60 to 70° C. under a reduced pressure of 0.15 mm Hg to distill off 7.8 g of an unreacted C$_{10}$ compound.

The obtained pale yellow liquid crude product (31.5 g) had a ratio of the objective compound (γ-adduct) to an isomeric by-product (α-adduct) of 99.5:0.5 as determined by HPLC and GLC. The conversion was 99% or above.

The crude product was purified by flash column chromatography using 1.0 kg of 200-mesh silica gel and a single solvent system of n-hexane to give 20.8 g of the objective compound as a colorless liquid (yield: 95.4%, purity: 99.5%).

elemental analysis: C$_{20}$H$_{32}$ (MW=272.476)

|  | C (%) | H (%) |
|---|---|---|
| calculated: | 88.16 | 11.84 |
| found: | 88.20 | 11.80 |

NMR (CDCl$_3$, δ): 6.38 (d, d, 1H), 5.0~5.3 (m, 7H), 2.25 (m, 4H), 2.0~2.15 (m, 8H)
Mass: M$^+$=272

EXAMPLE 26

Synthesis of 3-methylene-7,11-dimethyl-1,6,10-dodecatriene

The same procedure as that described in Example 25 was repeated except that 1.46 g of metallic magnesium, 100 ml of tetrahydrofuran, three droplets of ethylene dibromide, 7 g (0.06 mol) of prenyl chloride having a purity of 90%, 8.16 g (0.06 mol) of anhydrous zinc chloride, 0.2 g (1.05 mmol) of CuI, 14.6 g (0.06 mol) of 3-chloro-6-methylene-2-methyloctadiene-1,7 having a purity of 70%, 80 ml of tetrahydrofuran and 200 ml of a saturated aqueous solution of ammonium chloride were used. Thus, 11.2 g of the objective compound was obtained as a colorless liquid (yield: 91.4%, purity: 98.5%).

This liquid has a ratio of the objective compound (γ-adduct) to an isomeric by-product (α-adduct) of 9.7 : 0.3 as determined by HPLC. The conversion was 98.9%.

elemental analysis: C$_{15}$H$_{24}$ (MW=204.362)

|  | C (%) | H (%) |
|---|---|---|
| calculated: | 88.16 | 11.84 |
| found: | 88.19 | 11.81 |

NMR (CDCl$_3$, δ): 6.35 (d, d, 1H), 5.0~5.3 (m, 6H)
Mass: M$^+$=204

EXAMPLES 27 TO 33

The same procedure as that described in Example 25 or 26 was repeated except that the kind and molar ratio of the catalyst, the solvent and the reaction conditions were varied each as specified in Table 2. The results are given in Table 2.

TABLE 2

| Example No. | Zinc chloride | Allylic chloride | Catalyst/mol % | Solvent | Reaction condition | Conversion* (%) | Product* (α/γ) |
|---|---|---|---|---|---|---|---|
| 27 | (structure with ZnCl) | (structure with Cl) | CuCl/5 | tetrahydrofuran | −15° C.~−5° C./5 hr | 98 | 0.5/99.5 |
| 28 | " | " | CuCl$_2$/10 | tetrahydro- | " | 97 | 0.5/99.5 |

TABLE 2-continued

| Example No. | Zinc chloride | Allylic chloride | Catalyst/mol % | Solvent | Reaction condition | Conversion* (%) | Product* (α/γ) |
|---|---|---|---|---|---|---|---|
| 29 | " | " | CuBr/10 | furan tetrahydrofuran | " | 99 | 0.4/99.6 |
| 30 | " | " | CuI.(C$_6$H$_5$)$_3$P/5 | diethyl ether | −5° C.~−0° C./2 hr | 99.5 | 0.3/99.7 |
| 31 | " | " | Cu(CH$_3$COCH$_2$COO)$_2$/10 | tetrahydrofuran | " | 98 | 0.5/99.5 |
| 32 | 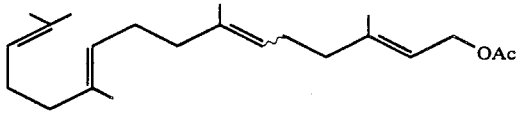 | " | CuBr.(CH$_3$)$_2$S/10 | diethyl ether | −15° C.~−5° C./5 hr | 97 | 0.4/99.6 |
| 33 | " | " | CuI.(C$_6$H$_5$)$_3$P/5 | tetrahydrofuran | " | 99 | 0.3/99.7 |

*The conversion is one as determined by HPLC based on the allylic chloride used as a raw material.
The α-adduct/γ-adduct ratio of the product is one in terms of HPLC value.

EXAMPLE 34

Synthesis of 3,7,11,15-tetramethylhexadeca-2(E),6,10(E),14(E)-tetraen-1-yl acetate

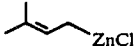

The same procedure as that described in Example 25 was repeated except that 1.46 g of metallic magnesium, 200 ml of tetrahydrofuran, three droplets of ethylene dibromide, 14.8 g (0.06 mol) of geranyl chloride having a purity of 70%, 5.4 g (0.04 mol) of anhydrous zinc chloride, 1 g (4.8 mmol) of CuBr·(CH$_3$)$_2$S, 8.8 g (0.04 mol) of 6-chloro-7-methylene-3-methyl-2(E)octen-1-yl acetate, 80 ml of tetrahydrofuran and 200 ml of a saturated aqueous solution of ammonium chloride were used. Thus, 10.9 g of the objective compound was obtained as a chlorless liquid (yield: 82.0%, purity: 97.9%).

This liquid had a ratio of the objective compound (γ-adduct) to an isomeric by-product (α-adduct) of 99.8 : 0.2 as determined by HPLC. The conversion was 99%.

elemental analysis: C$_{22}$H$_{36}$O$_2$ (MW=332.528)

| | C (%) | H (%) |
|---|---|---|
| calculated: | 79.46 | 10.91 |
| found: | 79.64 | 10.88 |

IR (cm$^{-1}$): 1740 (acetyl group)
NMR (CDCl$_3$, δ): 5.4 (t, 1H), 5.2 (m, 3H), 4.6 (d, 2H), 2.05 (s, 3H)
Mass: M$^+$=332

EXAMPLE 35

Synthesis of 3,7,11,15-tetramethylhexadeca-2(Z),6,10(E),14(E)-tetraen-1-yl acetate

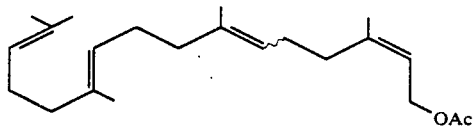

The same procedure as that described in Example 25 was repeated except that 0.73 g of metallic magnesium, 100 ml of tetrahydrofuran, three droplets of ethylene dibromide, 7.4 g (0.03 mol) of geranyl chloride having a purity of 70%, 4.08 g (0.03 mol) of anhydrous zinc chloride, 0.2 g (1.05 mmol) of CuI, 4.4 g (0.02 mol) of 6-chloro-7-methylene-3-methyl-2(Z)-octen-1-yl acetate, 80 ml of tetrahydrofuran and 100 ml of an aqueous solution of ammonium chloride were used. Thus, 6.1 g of the objective compound was obtained as a colorless liquid (yield: 91.7%, purity: 98.3%).

This liquid had a ratio of the objective compound γ-adduct) to an isomeric by-product (α-adduct) of 99.5 : 0.5 as determined by HPLC. The conversion was 98.6%.

elemental analysis: C$_{22}$H$_{36}$O$_2$ (MW=332.528)

| | C (%) | H (%) |
|---|---|---|
| calculated: | 79.46 | 10.91 |
| found: | 79.58 | 10.90 |

IR (cm$^{-1}$): 1740 (acetyl group)
NMR (CDCl$_3$, δ): 5.4 (t, 1H), 5.25 (m, 3H), 4.6 (d, 2H), 2.0 (s, 3H)
Mass: M$^+$=332

EXAMPLE 36

Synthesis of 3,7,11,15-tetramethylhexadeca-1,6,10(E),14(E)-tetraen-3-yl acetate

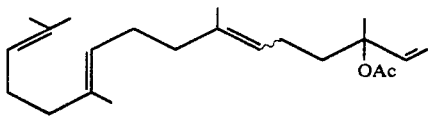

The same procedure as that described in Example 25 was repeated except that 0.73 g of metallic magnesium, 100 ml of tetrahydrofuran, three droplets of ethylene dibromide, 7.4 g (0.03 mol) of geranyl chloride having a purity of 70%, 4.08 g (0.03 mol) of anhydrous zinc chloride, 0.2 g (1.05 mmol) of CuI, 4.4 g (0.02 mol) of 6-chloro-7-methylene-3-methyl-1-octen-3-yl acetate, 80 ml of tetrahydrofraun and 100 ml of an aqueous solution of ammonium chloride were used. Thus, 5.7 g of the objective compound was obtained as a colorless liquid (yield: 85.7%, purity: 98.8%).

This liquid had a ratio of the objective compound (γ-adduct) to an isomeric by-product (α-adduct) of 99.7 : 0.3 as determined by HPLC. The conversion was 98.0%.

IR (cm$^{-1}$): 1740 (acetyl group)
NMR (CDCl$_3$, δ): 6.0 (d, d, 1H), 5.1~5.3 (m, 5H), 2.0 (s, 3H)
Mass: M$^+$=332

EXAMPLE 37

Synthesis of 3,7,11,15-tetramethylhexadeca-2(E),6(E),10,14(E)-tetraen-1-yl acetate

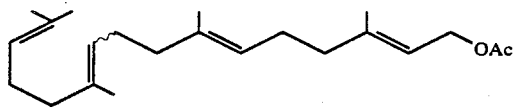

The same procedure as that described in Example 25 was repeated except that 0.73 g of metallic magnesium, 100 ml of tetrahydrofuran, three droplets of ethylene dibromide, 3.5 g (0.03 mol) of prenyl chloride having a purity of 90%, 4.08 g (0.03 mol) of anhydrous zinc chloride, 0.5 g (2.4 mmol) of CuBr·(CH$_3$)$_2$S, 6.0 g (0.02 mol) of 10-chloro-11-methylene-3,7-dimethyl-2(E),-6(E)-dodecadien-1-yl acetate, 80 ml of tetrahydrofuran, and 100 ml of a saturated aqueous solution of ammonium chloride were used. Thus, 4.8 g of the objective compound was obtained as a colorless liquid (yield: 72.2%, purity: 98.4%).

This liquid had a ratio of the objective compound (γ-adduct) to an isomeric by-product (α-adduct) of 99.5 : 0.5 as determined by HPLC. The conversion was 98.2%.

IR (cm$^{-1}$): 1740 (acetyl group)
NMR (CDCl$_3$, δ): 5.4 (t, 1H), 5.2 (m, 3H), 4.6 (d, 2H), 2.0 (s, 3H)
Mass: M$^+$=332

EXAMPLE 38

Synthesis of α-tocotrienyl benzyl ether

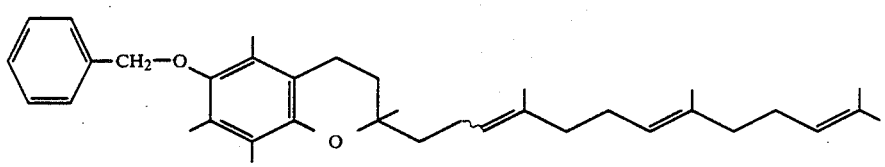

The same procedure as that described in Example 1 was repeated except that 0.73 g of metallic magnesium, 100 ml of tetrahydrofuran, three droplets of ethylene dibromide, 7.4 g (0.03 mol) of geranyl chloride having a purity of 70%, 4.08 g (0.03 mol) of anhydrous zinc chloride, 0.6 g (1.4 mmol) of CuI·(C$_6$H$_5$)$_3$P, 2 g (0.005 mol) of 2,5,7,8-tetramethyl-2-(3'-chloro-4'-methylenepentyl)-6-yl benzyl ether and 50 ml of tetrahydrofuran were used. Thus, 2.6 g of the objective compound was obtained as a colorless oil (yield: 95.5%, purity: 98.5%).

This oil had a ratio of the objective compound (γ-adduct) to an isomeric by-product (α-adduct) of 99.6:0.4 as determined by HPLC and GLC.

The IR and NMR data of the above oil were identical to those of the standard sample prepared separately.

EXAMPLE 39

Synthesis of 2-(4',8',12'-trimethyldodeca-3',7',11'-trienyl)-2,4-dimethyl-1,3-dioxolane

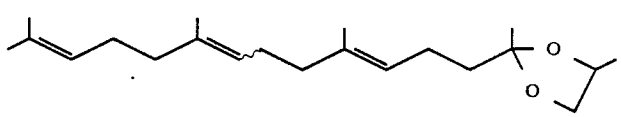

The same procedure as that described in Example 25 was repeated except that 0.36 g of metallic magnesium, 40 ml of tetrahydrofuran, three droplets of ethylene dibromide, 1.8 g (0.015 mol) of prenyl chloride having a purity of 90%, 2.1 g (0.015 mol) of anhydrous zinc chloride, 0.15 g (0.75 mmol) of CuBr·(CH$_3$)$_2$S, 1.43 g of 2-(7'-chloro-4'-8'-dimethyl-3'-8'-nonadienyl)-2,4-dimethyl-1,3-dioxolane and 30 ml of tetrahydrofuran were used. Thus, 0.92 g of the objective compound was obtained (yield: 57%).

The obtained product was deketalized and catalystically reduced into phytone to determine the α-adduct content by GLC. The content was 0.3% or below.

EXAMPLE 40

Synthesis of farnesylacetone

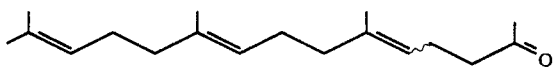

The same procedure as that described in Example 25 was repeated except that 0.73 g of metallic magnesium, 80 ml of tetrahydrofuran, three droplets of ethylene dibromide, 7.4 g (0.03 mol) of geranyl chloride having a purity of 70%, 4.1 g (0.03 mol) of anhydrous zinc chloride, 0.2 g of CuI, 3 g (0.02 mol) of 3-chloromethylheptenone and 30 ml of tetrahydrofuran were used. Thus, 4.1 g of the objective compound was obtained as a colorless liquid (yield: 78.2%, purity: 98.8%).

The obtained compound was catalytically reduced into phytone to determine the α-adduct content by GLC. The content was 0.3% by below.

EXAMPLE 41

Synthesis of 3-methylene-7,11,15-trimethyl-1,6,10(Z),14(E)-hexadecatetraene

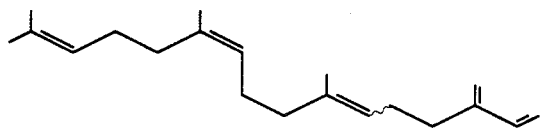

The same procedure as that described in Example 25 was repeated except that 0.73 g of metallic magnesium, 80 ml of tetrahydrofuran, three droplets of ethylene dibromide, 7.4 g (0.03 mol) of neryl chloride having a purity of 70%, 2.7 g (0.02 mol) of anhydrous zinc chloride, 0.2 g (1.05 mmol) of CuI, 4.4 g (0.02 mol) of 3-chloro-6-methylene-2-methyloctadiene-1,7 and 30 ml of tetrahydrofuran were used. Thus, 5.05 g of the objective compound was obtained as a colorless liquid (yield: 92.8%).

The liquid had a ratio of the objective compound (γ-adduct) to an isomeric by-product (α-adduct) of 99.6 : 0.4 as determined by HPLC. The conversion was 99.0%.

EXAMPLE 42

Synthesis of 3,7,11,15-tetramethylhexadeca-2(E),6,10(Z),14(E)-tetraen-1-yl acetate

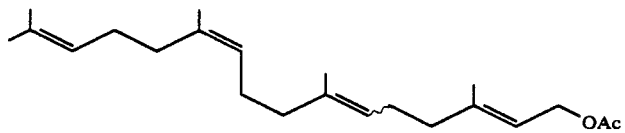

The same procedure as that described in Example 25 was repeated except that 1.46 g of metallic magnesium, 200 ml of tetrahydrofuran, five droplets of, ethylene dibromide, 14.8 g (0.06 mol) of neryl chloride having a purity of 70%, 5.4 g (0.04 mol) of anhydrous zinc chloride, 1 g (4.8 mmol) of CuBr·(CH$_3$)$_2$S, 8.8 g (0.04 mol) of 6-chloro-7-methylene-3-methyl-2(E)-octen-1-yl acetate and 80 ml of tetrahydrofuran were used. Thus, 11.1 g of the objective compound was obtained as a colorless liquid (yield: 83.5%, purity: 98.6%).

This liquid had a ratio of the objective compound (γ-adduct) to an isomeric by-product (α-adduct) of 99.8 : 0.2 as determined by HPLC. The conversion was 100%.

IR (cm$^{-1}$): 1740 (acetyl group)
NMR (CDCl$_3$, δ): 5.4 (t, 1H), 5.0~5.3 (m, 3H), 4.6 (d, 2H), 2.05 (s, 3H)
Mass: M$^+$ =332

EXAMPLE 43

Synthesis of 3,7,11,15-tetramethylhexadeca-2(Z),6,10(Z),14(E)-tetraen-1-yl acetate

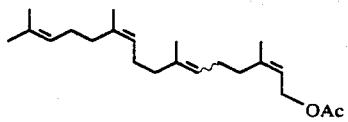

The same procedure as that described in Example 25 was repeated except that 0.73 g of metallic magnesium, 100 ml of tetrahydrofuran, three droplets of ethylene dibromide, 7.4 g (0.03 mol) of neryl chloride having a purity of 70%, 2.7 g (0.02 mol) of anhydrous zinc chloride, 0.3 g (0.7 mmol) of CuI·(C$_6$H$_5$)$_3$P, 4.4 g (0.02 mol) of 6-chloro-7-methylene-3-methyl-2(Z)-octen-1-yl acetate and 80 ml of tetrahydrofuran were used. Thus, 6.0 g of the objective compound was obtained as a colorless liquid (yield 90.2%, purity: 98.7%).

This liquid had a ratio of the objective compound (γ-adduct) to an isomeric by-product (α-adduct) of 99.8 : 0.2 as determined by HPLC. The conversion was 99.0%.

EXAMPLE 44

Synthesis of 3,7,11,15-tetramethylhexadeca-1,6,10(Z),14(E)-tetraen-3-yl acetate

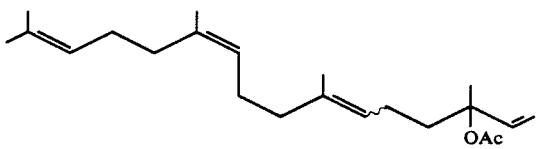

The same procedure as that described in Example 25 was repeated except that 0.73 g of metallic magnesium, 80 ml of tetrahydrofuran, three droplets of ethylene dibromide, 7.4 g (0.03 mol) of neryl chloride having a purity of 70%, 2.7 g (0.02 mol) of anhydrous zinc chloride, 0.2 g (1.05 mmol) of CuI, 4.4 g (0.02 mol) of 6-chloro-7-methylene-3 -methyl-1-octen-3-yl acetate and 60 ml of tetrahydrofuran were used. Thus, 5.9 g of the objective compound was obtained as a colorless liquid (yield: 88.7%, purity: 98.4%).

This liquid had a ratio of the objective compound (γ-adduct) to an isomeric by-product (α-adduct) of 99.8 : 0.2 as determined by HPLC. The conversion was 100%.

EXAMPLE 45

Synthesis of 3-methylene-7,11,15-trimethyl-1,6,10(E)-hexadeca-triene

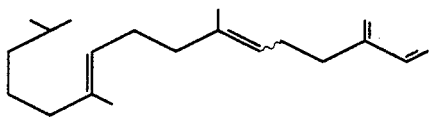

The same procedure as that described in Example 25 was repeated except that 0.73 g of metallic magnesium, 80 ml of tetrahydrofuran, three droplets of ethylene dibromide, 6.55 g (0.03 mol) of 6,7-dihydrogeranyl chloride, 2.7 g (0.02 mol) of anhydrous zinc chloride, 0.2 g (1.05 mmol) of CuI, 4.4 g (0.02 mol) of 3-chloro-6-methylene-2-methyl-octadiene-1,7 and 30 ml of tetrahydrofuran were used. Thus, 5.0 g of the objective compound was obtained as a colorless liquid (yield: 91.1%, purity: 99.2%).

The liquid had a ratio of the objective compound (γ-adduct) to an isomeric by-product (α-adduct) of 9.8:0.2 as determined by HPLC. The conversion was 99.5%.

EXAMPLE 46

Synthesis of 3,7,11,15-tetramethylhexadeca-2(E),6,10(E)-trien-1-yl acetate

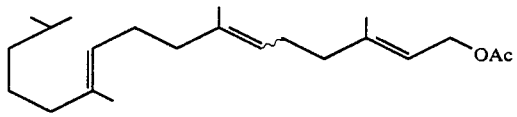

The same procedure as that described in Example 25 was repeated except that 0.73 g of metallic magnesium, 80 ml of tetrahydrofuran, three droplets of ethylene dibromide, 6.55 g (0.03 mol) of 6,7-dihydrogeranyl chloride having a purity of 80%, 2.7 g (0.02 mol) of anhydrous zinc chloride, 0.25 g (1.2 mmol) of CuBr·(CH₃)₂S, 4.4 g (0.02 mol) of 6-chloro-7-methylene-3-methyl-2(E)-octen-1-yl acetate and 40 ml of tetrahydrofuran were used. Thus, 5.7 g of the objective compound was obtained as a colorless liquid (yield: 85.2%, purity: 99.1%).

This liquid had a ratio of the objective compound (γ-adduct) to an isomeric by-product (α-adduct) of 99.8:0.2 ad determined by HPLC. The conversion was 100%.

EXAMPLE 47

Synthesis of 15-chloro-3-methylene-7,11,15-trimethylhexadeca-1,6,10(E)-triene

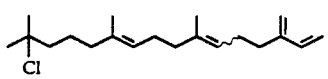

The same procedure as that described in Example 25 was repeated except that 0.73 g of metallic magnesium, 100 ml of tetrahydrofuran, five droplets of ethylene dibromide, 8.37 g (0.03 mol) of 1,7-dichloro-3,7-dimethyloct-2(E)-ene, 2.7 g (0.02 mol) of anhydrous zinc chloride, 0.2 g (1.05 mmol) of CuI, 4.4 g (0.02 mol) of 3-chloro-6-methylene-2-methyloctadiene-1,7 and 40 ml of tetrahydrofuran were used. Thus, 5.4 g of the objective compound was obtained as a colorless liquid (yield: 87.4%, purity: 98.6%).

This liquid had a ratio of the objective compound (γ-adduct) to an isomeric by-product (α-adduct) of 99.7:0.3 as determined by HPLC. The conversion was 99.2%.

COMPARATIVE EXAMPLE 2

Synthesis of 15-chloro-3-methylene-7,11,15-trimethylhexadeca-1,6,10(E)-triene

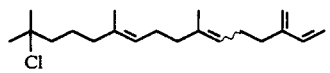

objective compound (γ-adduct)

0.73 g of metallic magnesium, 100 ml of tetrahydrofuran and five droplets of ethylene dibromide were introduced into a 500-ml four-necked flask purged with argon gas. While stirring the contents under cooling at −150° C. with a freezing mixture, 30 ml of a tetrahydrofuran solution containing 8.37 g (0.03 mol) of 1,7-dichloro-3,7-dimethyloct-2(E)-ene having a purity of 75% was gradually dropped into the flask over a period of 3 hours. After the completion of the dropping, the resulting contents were stirred at that temperature for 2 hours to thereby dissolve the metallic magnesium. Thus, a light gray solution of a Grignard reagent in 1,7-dichloro-3,7-dimethyloct-2(E)-ene was obtained.

0.2 g (1.05 mmol) of CuI was added to this solution, followed by the stirring at −15° C. for 30 minutes. 40 ml of a tetrahydrofuran solution of 4.4 g (0.02 mol) of 3-chloro-6-methylene-2-methyloctadiene-1,7 having a purity of 70% was dropped into the flask over a period of 30 minutes. After the completion of the dropping, the contents were stirred at that temperature for 3 hours. After the confirmation of the disappearance of the chloride as the starting material by TLC and HPLC, the subsequent procedure was conducted in a similar manner to that described in Example 25 to obtain 4.1 g of a colorless liquid (yield: 66.3%).

This liquid had a ratio of the objective compound (γ-adduct) to an isomeric by-product (α-adduct) of 89.5 : 10.5 as determined by HPLC. The conversion was 85%.

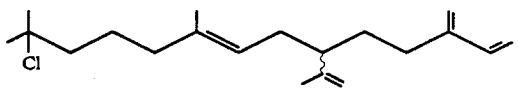

isomeric by-product (α-adduct)

We claim:
1. A process for producing a terpene compound having the formula (III), which comprises reacting an allylic halide having the formula (I) with a Grignard reagent having the formula (II) in the presence of anhy- drous zinc chloride and a copper compound or an organic zinc halide compound having the formula (IV) in the presence of a copper compound, provided that when A-A is C-C, R' is hydrogen and when A-A is C=C, X is chlorine.

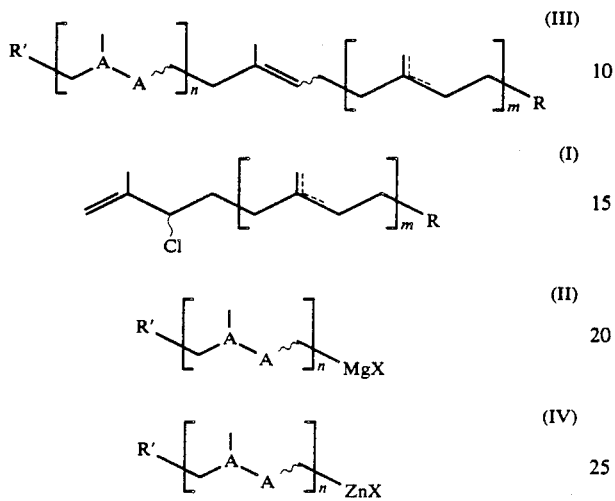

[wherein R represents a group represented by the formula:

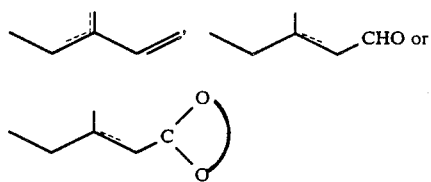

(wherein the

group represents a heterocyclic group containing two oxygen atoms as heteroatoms), a group represented by the formula:

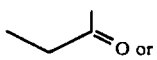

or

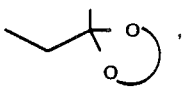

a hydroxyl group, a group represented by the formula: -OR$_1$ (wherein R$_1$ represents an acetyl (Ac) group, a propionyl group or a benzyl, methoxymethyl or tetrahydrofurfuryl group), a group represented by the formula:

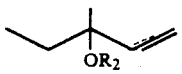

(wherein R$_2$ represents a hydrogen atom or an Ac group), a group represented by the formula:

(wherein R$_3$ represents a hydrogen atom or a methyl or ethyl group), a group represented by the formula:

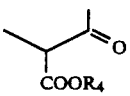

(wherein R$_4$ represents a methyl or ethyl group), a group represented by the formula:

(wherein R$_5$ and R$_6$ may be the same or different from each other and each represent a hydrogen atom or a methyl ethyl or isopropyl group), a group represented by the formula:

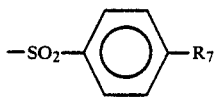

(wherein R$_7$ represents a hydrogen atom or a methyl group) or a group represented by the formula:

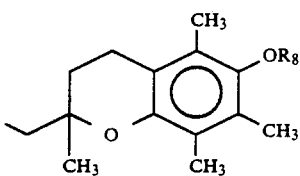

(wherein R$_8$ represents a hydrogen atom or a hydroxyl-protective group); R' represents a hydrogen atom or a straight-chain or branched alkyl, alkoxyalkyl, aralkyl, cyclic alkyl or halogen-substituted alkyl group; m represents 0 to 3, n is 1 to 3, A-A is C-C or C=C and X is bromine or chlorine].

2. The process as claimed in claim 1, in which A-A is C-C.

3. The process as claimed in claim 1, in which A-A is C=C.

4. The process as claimed in claim 1, in which the copper compound is present in an amount of $10^{-5}$ to $10^{-1}$ gram atom per reaction equivalent.

5. The process as claimed in claim 1, in which the copper compound is selected from the group consisting of inorganic copper salts, organic copper salts and copper complex salts.

6. The process as claimed in claim 1, in which the copper compound is selected from the group consisting of CuI, CuBr, CuCl, CuCl$_2$, Cu(CH$_3$COCH$_2$COO)$_2$, CuI·P(C$_2$H$_5$)$_3$, CuI·P(C$_6$H$_5$)$_3$, CuBr·(CH$_3$)$_2$S and Li$_2$CuCl$_4$.

* * * * *

UNITED STATES PATENT AND TRADEMARK OFFICE
CERTIFICATE OF CORRECTION

PATENT NO. : 5 073 659
DATED : December 17, 1991
INVENTOR(S) : Kichisaburo HAMAMURA et al It is certified that error appears in the above-identified patent and that said Letters Patent is hereby corrected as shown below:

On the title page, item (75) Inventors: change "Yoshihiro" to ---Yoshihiko---.

In the Abstract, line 8; change "A-A is CC" to --A-A is C=C--.

Column 35, line 5; change "chlorine." to ---chlorine,---.

Signed and Sealed this

Fifteenth Day of June, 1993

Attest:

MICHAEL K. KIRK

Attesting Officer    Acting Commissioner of Patents and Trademarks